United States Patent
Caclin

(10) Patent No.: US 11,077,253 B2
(45) Date of Patent: Aug. 3, 2021

(54) SYRINGE

(71) Applicant: GUERBET, Villepinte (FR)

(72) Inventor: Jérôme Caclin, Saint Symphorien d'Ozon (FR)

(73) Assignee: Guerbet, Villepinte (FR)

( * ) Notice: Subject to any disclaimer, the term of this patent is extended or adjusted under 35 U.S.C. 154(b) by 122 days.

(21) Appl. No.: 15/775,726

(22) PCT Filed: Nov. 10, 2016

(86) PCT No.: PCT/EP2016/077307
§ 371 (c)(1),
(2) Date: May 11, 2018

(87) PCT Pub. No.: WO2017/081178
PCT Pub. Date: May 18, 2017

(65) Prior Publication Data
US 2018/0326156 A1 Nov. 15, 2018

(30) Foreign Application Priority Data

Nov. 12, 2015 (FR) ...................................... 1560823

(51) Int. Cl.
*A61M 5/31* (2006.01)
(52) U.S. Cl.
CPC ........ *A61M 5/3137* (2013.01); *A61M 5/3129* (2013.01); *A61M 5/3135* (2013.01); *A61M 5/3148* (2013.01); *A61M 2205/586* (2013.01)
(58) Field of Classification Search
CPC .............. A61M 5/3137; A61M 5/3129; A61M 5/3135; A61M 2205/586; A61M 5/3148; A61M 2005/3131
See application file for complete search history.

(56) References Cited

U.S. PATENT DOCUMENTS 2,658,511 A    11/1953   Furnell
3,958,570 A *   5/1976   Vogelman ............... A61M 5/24
                                                         604/206
(Continued)

FOREIGN PATENT DOCUMENTS

CN       101252961 A      8/2008
CN       102218176 A     10/2011
(Continued)

OTHER PUBLICATIONS

International search report for PCT/EP2016/077307 dated Feb. 24, 2017.
(Continued)

*Primary Examiner* — Lauren P Farrar
*Assistant Examiner* — Hamza A Darb
(74) *Attorney, Agent, or Firm* — Thompson Coburn LLP; Steven M. Ritchey

(57) ABSTRACT

This syringe (1) comprises an elongate hollow body (3) forming a reservoir intended to contain a substance to be injected, the body (3) comprising a tip intended to receive a connection device and an opening (32) located at the opposite side of the body (3) relative to the tip, a piston mounted sliding in the body (3) and movable in translation along a longitudinal axis (X3) of the syringe between a retracted position, in which the piston is in abutment at the tip side, and an extended position, in which the piston is in abutment at the opening side (32), gripping members (34, 36) provided on the body (3), and a gripping member (50) provided at an opposite end of the piston relative to a head of the piston. The gripping members (34, 36) provided on the body (3) comprise bearing areas (34a, 36a) for fingers of a user, oriented towards the gripping member (50) of the piston, and the gripping member (50) of the piston comprises at least one bearing area for fingers of the user, located facing the (Continued)

gripping members (34, 36) provided on the body (3). The piston (5) is formed from a single piece made from a material having a Young's modulus greater than 3000 MPa and the piston (5) has no elastic area between the gripping member (50) of same and the substance to be injected.

11 Claims, 4 Drawing Sheets

(56) References Cited

U.S. PATENT DOCUMENTS

| | | | |
|---|---|---|---|
| 4,929,238 A * | 5/1990 | Baum | A61M 25/10182 |
| | | | 604/118 |
| 5,318,534 A | 6/1994 | Williams et al. | |
| 6,616,634 B2 | 9/2003 | Benz et al. | |
| 7,713,244 B1 * | 5/2010 | Cherif Cheikh | A61M 5/002 |
| | | | 604/187 |
| 8,412,310 B2 | 4/2013 | Liu et al. | |
| 2002/0051553 A1 * | 5/2002 | Moriguchi | H04R 7/00 |
| | | | 381/369 |
| 2002/0087125 A1 | 7/2002 | Pokorney | |
| 2003/0097096 A1 | 5/2003 | Niedospial | |
| 2009/0137966 A1 | 5/2009 | Rueckert et al. | |
| 2010/0211007 A1 * | 8/2010 | Lesch, Jr. | A61B 17/24 |
| | | | 604/97.02 |
| 2011/0008750 A1 * | 1/2011 | Dillard, III | A61M 5/3257 |
| | | | 433/90 |

FOREIGN PATENT DOCUMENTS

| | | |
|---|---|---|
| CN | 102316924 A | 1/2012 |
| DE | 9200443 U1 | 3/1992 |
| EP | 2623143 A1 | 8/2013 |
| JP | 58-182749 U | 12/1983 |
| JP | 1-90551 U | 6/1989 |
| JP | 2007175444 A | 7/2007 |
| JP | 2012525231 A | 10/2012 |
| RU | 2459639 C2 | 8/2012 |
| WO | 2007027585 A2 | 3/2007 |
| WO | 2010096294 A1 | 8/2010 |
| WO | 2010127146 A1 | 11/2010 |

OTHER PUBLICATIONS

Office Action for CN Application 2016800658973 dated Apr. 26, 2020 and English translation.
Office Action for JP Application 2018-524273 dated Dec. 8, 2020 and English translation.
Office Action for RU Application 2018117391 dated Mar. 6, 2020 and English translation.

* cited by examiner

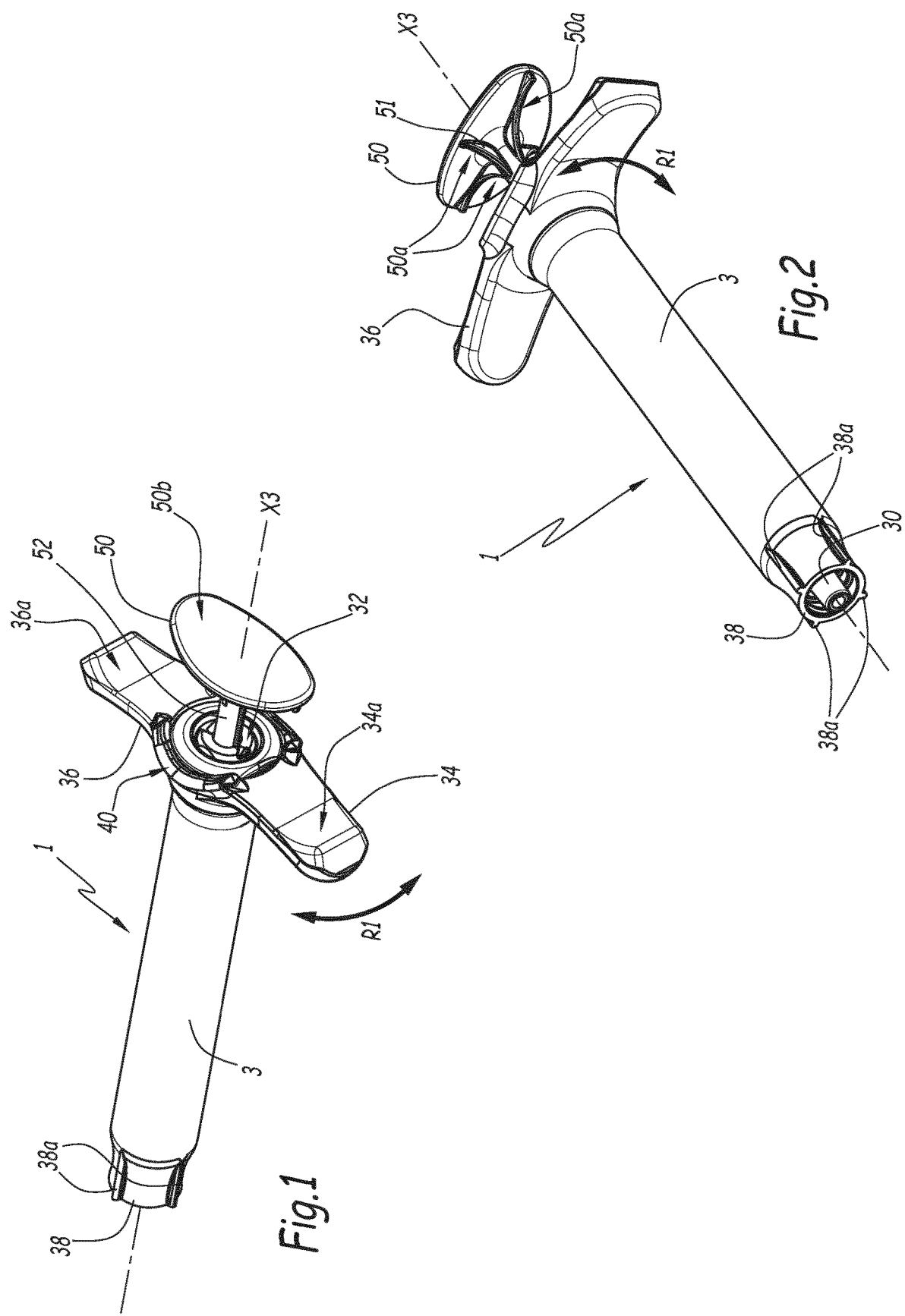

SYRINGE

CROSS-REFERENCE TO RELATED APPLICATIONS

This application is a U.S. National Phase application of PCT/EP2016/077307, filed on Nov. 10, 2016, which claims the benefit of FR Application No. 1560823, filed on Nov. 12, 2015, both of which are incorporated herein by reference in their entireties.

The invention relates to a syringe.

Manual syringes are used by medical personnel to inject a pressurized fluid during a medical procedure, especially in interventional radiology. Syringes of this kind can be used in the case of repetitive procedures involving filling and injection, or in the case of injections through a small catheter or microcatheter. Such syringes comprise a hollow body containing the substance to be injected into the patient, an injection piston, and gripping means provided on the body and on the piston.

The syringes known in particular from U.S. Pat. Nos. 6,616,634 and 8,412,310 do not permit easy filling with one hand, and they use cumbersome gripping means. In addition, with syringes of this kind, the end of the injection is not very practical, since the practitioner's thumb, which bears on the piston, arrives at a plane close to that formed by the index finger and the middle finger, which results in less effective control of the end of the injection.

During use of most syringes of the prior art, the information relating to the injection forces, which are supplied by the user in order to inject a substance contained in these syringes, is not transmitted sufficiently to the user via his contact with the gripping member of said syringes. Therefore, the person using the syringe cannot finely adjust the force applied by him according to the information he receives during the injection.

It is these disadvantages that the invention is intended more particularly to overcome by making available a novel syringe whose manipulation is more practical.

To this end, the invention relates to a syringe comprising:
- an elongate hollow body forming a reservoir intended to contain a substance to be injected, the body comprising a tip intended to receive a connection device, and an opening located at the opposite end of the body relative to the tip,
- a piston mounted slidably in the body and movable in translation along a longitudinal axis of the syringe between a retracted position, in which the piston is in abutment at the tip, and an extended position, in which the piston is in abutment at the opening,
- gripping members provided on the body, and a gripping member provided at an opposite end of the piston relative to a head of the piston.

This syringe is characterized in that the gripping members provided on the body comprise bearing zones for fingers of a user, which bearing zones are oriented toward the gripping member of the piston, in that the gripping member of the piston comprises at least one bearing zone for fingers of the user, which bearing zone is located facing the gripping members provided on the body, in that the piston is formed as a single piece made from a material having a Young's modulus greater than 3000 MPa, and in that the piston has no elastic zone between its gripping member and the substance to be injected.

By virtue of the invention, the syringe can be easily used with one hand for injecting and filling, and the practitioner can easily adjust his hold of the syringe by virtue of the possibility of rotation of the gripping members that are provided on the body and on the finger-rest of the piston.

According to advantageous but non-obligatory aspects of the invention, such a syringe can incorporate one or more of the following features, in any technically admissible combination:
- The piston is movable in rotation with respect to the body about the longitudinal axis of the syringe.
- The gripping member of the piston comprises a bearing zone located facing away from the head of the piston.
- The tip of the body comprises a peripheral flange, an external surface of which is provided with gripping ribs extending parallel to the longitudinal axis of the syringe.
- The bearing zone of the gripping member of the piston, located facing the gripping members provided on the body, comprises concave formations provided on each side of the rod of the piston.
- In the retracted position of the piston, the gripping member of the piston is spaced apart from the gripping members, provided on the body, by a distance at least equal to 15 mm.
- The bearing zones of the gripping members provided on the body comprise concave formations provided on each side of the opening of the hollow body and facing the bearing zone of the piston, these concave formations being configured on two radial tabs, which each form one of the gripping members provided on the body.
- The gripping members provided on the body are configured on one piece, this piece being mounted rotatably on the body about the longitudinal axis of the syringe.
- The two concave bearing zones are configured on the piece on which the gripping members provided on the body are configured, on the parts that connect these gripping members.
- The two concave bearing zones are oriented in the direction of the gripping member, allowing a finger of the user to bear in a radial direction with respect to the longitudinal axis of the syringe.
- The gripping member of the piston has an oval shape.

The invention will be better understood, and other advantages thereof will become more clearly apparent, in light of the following description of a syringe in accordance with its principle, said description being given by way of non-limiting example and with reference to the attached drawings, in which:

FIG. 1 is a perspective view of a syringe according to the invention,

FIG. 2 is a perspective view, at another angle, of the syringe from FIG. 1,

Figure 4:
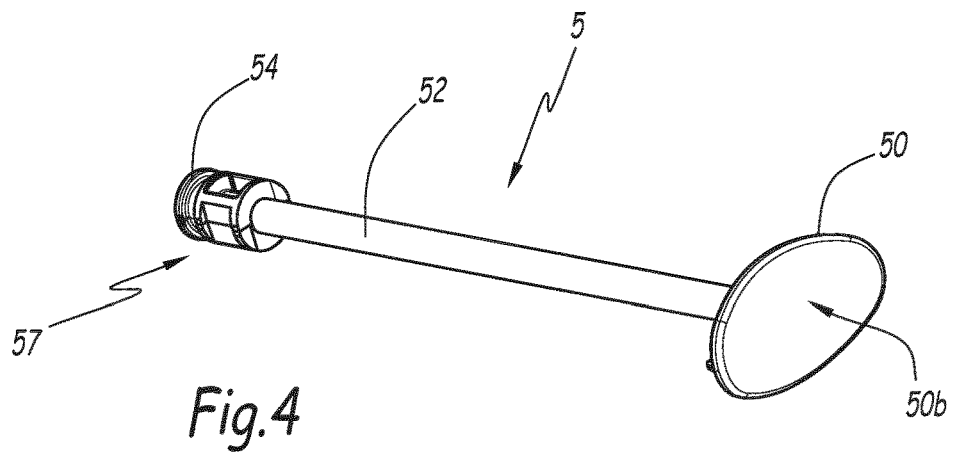
FIG. 4 is a perspective view of a piston of the syringe from FIGS. 1 to 3.
Figure 5:
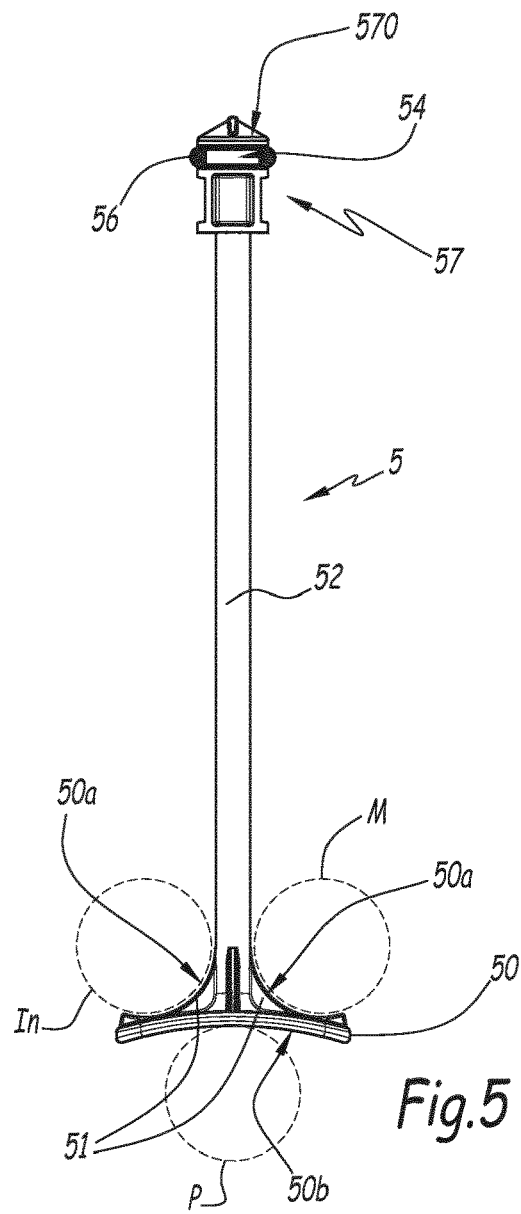
Figure 6:
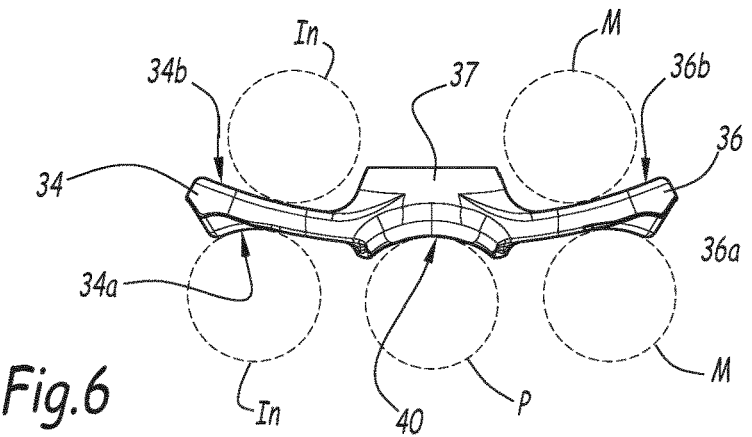
Figure 7:
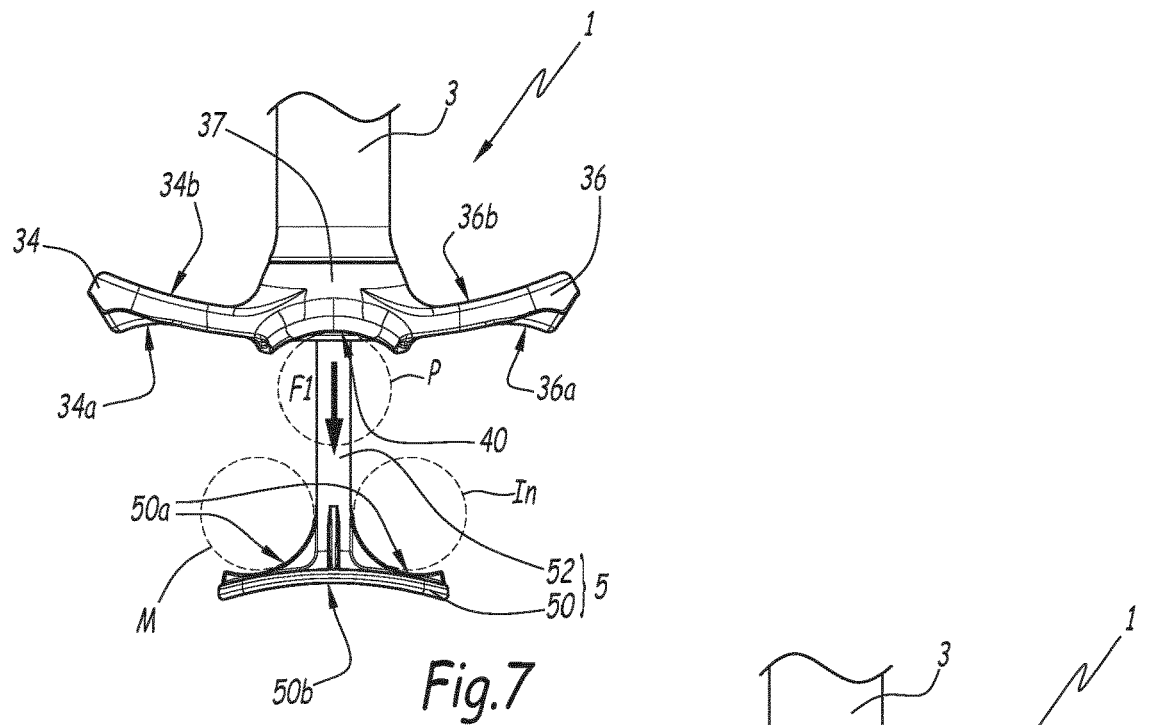
Figure 8:
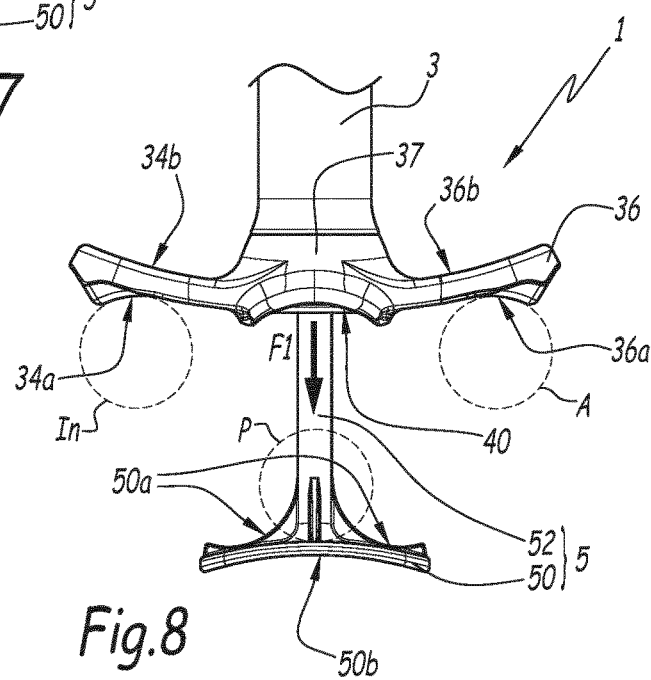

FIG. 5 is a side view of the piston from FIG. 4, with finger positions represented by circles drawn in broken lines, FIG. 6 is a side view of a gripping member of the syringe from FIG. 1, with finger positions represented by circles drawn in broken lines, FIG. 7 is a side view of part of the syringe from FIG. 1, in a second configuration, with the finger positions represented by circles drawn in broken lines, FIG. 8 is a view similar to FIG. 7, with different finger positions represented by circles drawn in broken lines.

FIG. 1 shows a syringe 1 suitable for manipulation by hand. The syringe 1 comprises an elongate hollow body 3 centered on a longitudinal axis X3, which also forms a longitudinal axis of the syringe 1. The body 3 forms a reservoir intended to contain substances that are to be injected. The body 3 comprises a tip 30 intended to receive a connection device. This tip 30 can advantageously be a Luer cone, the Luer connection complying with standards such as ISO 594 and ISO 80369, although the mention of these standards is not limiting. At the opposite end of the body 3 from the tip 30, the body 3 comprises an opening 32.

Figure 3:
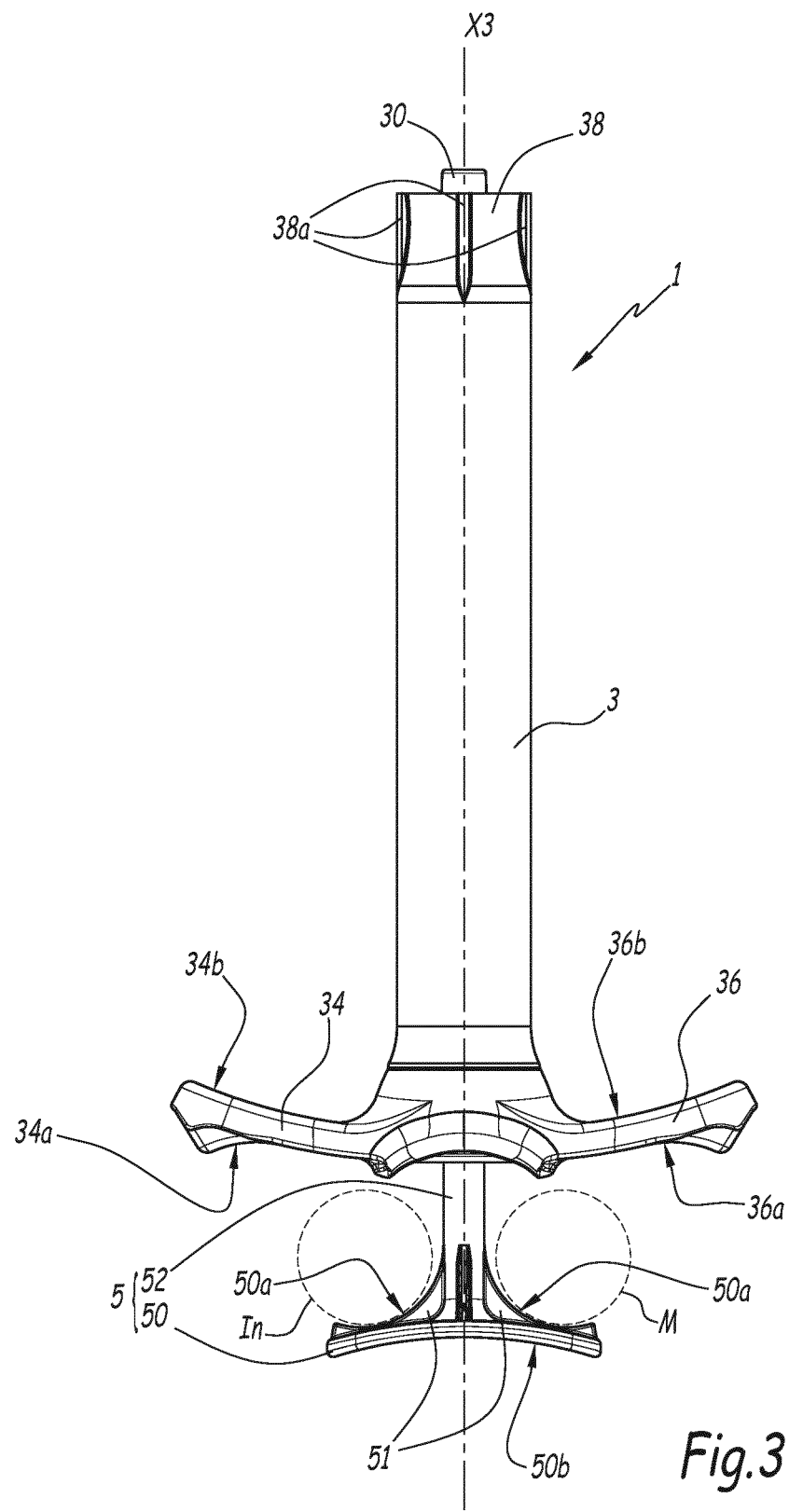
FIG. 3 is a side view of the syringe from FIGS. 1 and 2.

The syringe 1 likewise comprises a piston 5 mounted in the body 3 so as to be movable in translation along the axis X3 between a retracted position, shown in FIGS. 1 and 3, in which the piston 5 is in abutment at the tip 30, and an extended position, in which the piston 5 is in abutment at the opening 32. The piston 5 comprises a rod 52 which protrudes from the body 3 via the opening 32 of the syringe 1. At one of its ends, the piston 5 comprises a head 57 suitable for being placed in contact with a substance to be injected present in the body 3, and, at the other of its ends, it has a gripping member 50. The syringe 1 is shown in FIGS. 7 and 8 in an intermediate position, in which the piston 5 is partially extended from the body 3. The piston 5 is movable in rotation with respect to the body 3 about the longitudinal axis X3 of the syringe.

The syringe 1 comprises gripping members which allow a practitioner to manipulate the syringe in order to fill it with a substance and in order to administer the substance to a patient. For this purpose, the body 3 comprises gripping members 34 and 36 which are provided around the opening 32 and which are each formed by a tab extending radially with respect to the axis X3. The gripping member 50 provided at the opposite end of the piston 5 relative to the head 57 is included in the gripping members of the syringe 1. The gripping member 50 is formed by an oval plate which generally extends radially with respect to the rod 52.

Preferably, the gripping members 34 and 36 provided on the body 3 are movable in rotation, with respect to the body 3, about the axis X3 of the syringe 1.

According to the invention, the gripping members 34 and 36 provided on the body 3 comprise bearing zones 34a and 36a for a user's fingers, these bearing zones being oriented in the direction of the gripping member 50 of the piston 5, and the gripping member 50 of the piston 5 comprises at least one bearing zone 50a for fingers of the user, which bearing zone 50a is located facing the gripping members 34 and 36 of the body 3. The bearing zones 34a and 36a comprise concave formations provided on each side of the opening 32 of the body 3, on each of the gripping members 34 and 36.

This combination of features allows the user's fingers to be placed between the gripping members 34 and 36 and the gripping member 50 in such a way as to allow the syringe 1 to be manipulated with just one hand while filling it, that is to say when the piston 5 is progressively extended from the elongate body 3 according to the arrow F1, in such a way as to aspirate a substance in the reservoir of the syringe 1. The possibility of rotation (indicated by the double arrows R1) of the gripping members 34 and 36 with respect to the body 3 allows the user more comfortable positioning of his hand and fingers depending on his position with respect to the patient and allows him to manipulate the syringe 1 more easily and more safely.

The gripping members 34 and 36 are preferably configured on one piece 37 which is mounted rotatably on the body 3 about the axis X3. The piece 37 is preferably manufactured independently from the body 3. The piece 37 is preferably fitted onto the body 3 from the direction of the tip 30 as far as the opening 32 and is fixed on this opening 32 by clipping. The piece is preferably fixed on the body 3 by elastic deformation of this piece.

The bearing zone 50a comprises concave formations provided on each side of the rod 52. These concave formations are preferably configured on ribs 51 which connect the rod 52 to the gripping member 50. The piston 5 preferably comprises four ribs 51, which form the bearing zones 50a oriented at 90° to one another about the rod 52.

The body 3 also comprises two concave bearing zones 40 which are provided on the perimeter of the opening 32 and are situated between the gripping members 34 and 36. These concave bearing zones 40 are oriented in the direction of the gripping member 50 and support a finger of the user in a radial direction with respect to the axis X3. The bearing zones 40 are preferably configured on the piece 37, on the parts which connect the gripping members 34 and 36. The bearing zones 40 are advantageously formed by rounded beads centered on the axis X3.

Thus, when filling the syringe 1, a thumb P of the user can be placed against one of the bearing zones 40, while a middle finger M and an index finger In of the user are placed on the bearing zones 50a of the piston 5. This positioning of fingers is represented in FIG. 7.

Alternatively, during filling of the syringe 1, the thumb P of the user can be placed on the bearing zone 50a, while a ring finger A of the user and the index finger In are placed respectively on the bearing zones 34a and 36a. This positioning of fingers is represented in FIG. 8.

The gripping members 34 and 36 likewise comprise bearing zones 34b and 36b situated opposite the bearing zones 34a and 36a, that is to say oriented in the direction of the tip 30 of the body 3. The bearing zones 34b and 36b are used for placing the index finger In and the middle finger M during the injection of a substance.

In the first retracted position of the piston 5, the gripping member 50 is spaced apart from the gripping members 34 and 36 by a distance at least equal to 15 mm, preferably at least equal to 20 mm. This means that, when the injection of a product into a patient has been completed, the user's fingers placed on the gripping members 34 and 36 and the user's thumb placed on the piston 5 are not brought too close together, such that the user is able to better control his maneuver and his hold on the syringe 1. This likewise permits the placement of the user's fingers, for example the index finger In and the middle finger M, between the piston 5 and the body 3 when the syringe 1 has to be filled again, as is shown in FIG. 3.

The head 57 of the piston 5 preferably comprises a peripheral groove 54 and an O-ring seal 56 mounted in the groove 54 and extending between the piston 5 and an inner wall of the body 3, in such a way as to ensure the leaktightness of the syringe 1. This embodiment is illustrated in FIG. 5.

The piston 5 preferably has no elastic zone between the gripping member 50 and the injectable substance with which the head 57 of the piston 5 is in contact.

The piston 5 is preferably designed as one very rigid piece, preferably made of a material having a Young's modulus of greater than 3000 MPa, more preferably greater than 7000 MPa, still more preferably greater than 11000 MPa. By virtue of the rigidity of the piston and by virtue of the latter being designed in one piece, the information relating to the injection forces, which is preferably tactile information, is transmitted directly to the hand of the user, which thus allows the latter to control the manipulation of the syringe and to better control the injection. In addition, the use of the O-ring seal 56 on the head 57 of the piston 5 makes it possible to do without a plastic sealing body at the end of the piston 5 that is in contact with the substance to be injected, as is generally the case in the prior art. A plastic sealing body and/or the use of a piston composed of several pieces and/or of a piston made of a less rigid material has the major disadvantage of creating one or more zones, in particular elastic zones, along the longitudinal axis X3 between the substance to be injected and the user's thumb, in which elastic zones some of the tactile information relating to the injection forces is lost.

More preferably still, the piston 5 is designed in one piece and made of a material having a Young's modulus of greater than 3000 MPa, and this piston 5 has no elastic zone between its gripping member 50 and the substance to be injected. In other words, the piston 5 does not comprise parts that are able to deform appreciably along the longitudinal axis X3 between the gripping member 50 and a surface 570 of the head 57 designed to be in contact with the substance to be injected. Thus, in these preferred embodiments, the tactile information relating to the injection forces is preserved and is therefore felt directly by the user.

The gripping member 50 comprises a bearing zone 50b located facing away from the head 57 of the piston 5. In the example shown, this bearing zone 50b is concave, which provides support for the thumb P for example. According to an embodiment that is not shown, this bearing zone 50b can be convex, which allows the palm of the hand to be used push the piston 5 into the body 3.

The tip 30 is surrounded by a peripheral flange 38, of which an external surface is provided with gripping ribs 38a which extend parallel to the axis X3. These gripping ribs permit rotation of the syringe 1 with the aid of the fingers, for example when a Luer connector has to be fitted onto the tip 30.

The invention claimed is:

1. A syringe comprising:
    an elongate hollow body forming a reservoir intended to contain a substance to be injected, the hollow body comprising a tip intended to receive a connection device, and an opening located at an opposite end of the hollow body relative to the tip;
    a one-piece piston comprising a head, a rod, a gripping member at an opposite end of the one-piece piston relative to the head of the one-piece piston, and four ribs that connect said rod to said gripping member, wherein the one-piece piston is mounted slidably in the hollow body and movable in translation along a longitudinal axis of the syringe between a retracted position, in which the head of the one-piece piston is in abutment at the tip, and an extended position, in which the head of the one-piece piston is in abutment at the opening, wherein the head of the one-piece piston comprises:
        a surface configured to be in contact with the substance to be injected; and
        a peripheral groove configured to receive an o-ring seal, wherein said peripheral groove is located, along said longitudinal axis of the syringe, inward from the surface configured to be in contact with the substance to be injected;
    wherein the one-piece piston is made from a material having a Young's modulus greater than 3000 MPa such that the one-piece piston has no elastic zone, along the longitudinal axis of the syringe, from the gripping member to the surface to be in contact with the substance to be injected;
    the o-ring seal mounted in the peripheral groove of the head, wherein the o-ring seal is configured to extend between the one-piece piston and an inner wall of the hollow body; and
    gripping members provided on the hollow body;
    wherein the gripping members provided on the hollow body comprise bearing zones for fingers of a user, the bearing zones are oriented toward the gripping member of the one-piece piston; and
    wherein the gripping member of the one-piece piston comprises bearing zones for fingers of the user, the bearing zones of the one-piece piston are located facing the gripping members provided on the hollow body and comprise concave formations provided on the ribs on each side of the rod of the one-piece piston such that said concave formations form said bearing zones of the one-piece piston oriented at 90° to one another about the rod.

2. The syringe as claimed in claim 1, wherein the one-piece piston is movable in rotation with respect to the hollow body about the longitudinal axis of the syringe.

3. The syringe as claimed in claim 1, wherein the gripping member of the one-piece piston comprises one bearing zone of the at least one bearing zone located facing away from the head of the one-piece piston.

4. The syringe as claimed in claim 1, wherein the tip of the hollow body comprises a peripheral flange, an external surface of which is provided with gripping ribs extending parallel to the longitudinal axis of the syringe.

5. The syringe as claimed in claim 1, wherein, in the retracted position of the one-piece piston, the gripping member of the one-piece piston is spaced apart from the gripping members, provided on the hollow body, by a distance at least equal to 15 mm.

6. The syringe as claimed in claim 1, wherein the bearing zones of the gripping members provided on the hollow body comprise concave formations provided on each side of the opening of the hollow body and facing the bearing zone of the one-piece piston, the concave formations being configured on two radial tabs, which each form one of the gripping members provided on the hollow body.

7. The syringe as claimed in claim 1, wherein the gripping members provided on the hollow body are configured on a piece that is mounted rotatably on the hollow body about the longitudinal axis of the syringe.

8. The syringe as claimed in claim 7, wherein the piece, to which the gripping members provided on the hollow body are configured, comprises parts that connect said gripping members and two concave bearing zones configured on the parts that connect said gripping members.

9. The syringe as claimed in claim 7, wherein the two concave bearing zones are oriented in a direction of the gripping member, allowing a finger of the user to bear in a radial direction with respect to the longitudinal axis of the syringe.

10. The syringe as claimed in claim 7, wherein the gripping member of the one-piece piston has an oval shape that is perpendicular to the longitudinal axis of the syringe.

11. The syringe as claimed in claim 1, wherein the concave formations provided on each side of the rod of the one-piece piston are configured on ribs that connect the rod to the gripping member of the one-piece piston.

* * * * *